United States Patent [19]

Snoble

[11] 4,281,200
[45] Jul. 28, 1981

[54] CATALYTIC PROCESS FOR CONVERTING OXAZOLIDINONES TO THEIR CORRESPONDING AMINOALCOHOLS

[75] Inventor: Karel A. J. Snoble, Midland, Mich.

[73] Assignee: The Dow Chemical Company, Midland, Mich.

[21] Appl. No.: 71,208

[22] Filed: Aug. 30, 1979

[51] Int. Cl.$^3$ .................... C07C 91/04; C07C 51/56
[52] U.S. Cl. .................................. 564/487; 548/229
[58] Field of Search .................... 260/584 R; 548/229; 423/229, 243; 564/487

[56] References Cited

U.S. PATENT DOCUMENTS

| 3,658,462 | 4/1972 | Van Scoy ........................ 564/487 |
| 4,138,468 | 2/1979 | Kettner et al. .................. 564/487 |

FOREIGN PATENT DOCUMENTS 1203874  9/1970  United Kingdom .

*Primary Examiner*—Patrick Garvin
*Assistant Examiner*—Raymond K. Covington
*Attorney, Agent, or Firm*—G. R. Baker

[57] ABSTRACT

A process for recovering amino alcohols, e.g. diisopropanolamine, from their corresponding cyclic reaction products, which products are the result of the reaction of $CO_2$ and the amino alcohol, i.e., oxazolidinones, a situation commonly encountered in acid gas removal processes employing the amino alcohols alone or in combination with other liquids such as sulfolane (tetrahydrothiophene-1,1-dioxide) for example, by reacting the cyclic product with a small but catalytic amount (less than about 10 mol percent) of a base metal compound such as the hydroxide or a base which will convert into a hydroxide under the conditions of reaction, i.e. the acid carbonates, carbonates, metaborates, oxides or hydrides at temperatures above about 105° C. to about the atmospheric boiling point of the reaction medium and, optionally, recovering the amino alcohol from the reaction mass.

11 Claims, No Drawings

CATALYTIC PROCESS FOR CONVERTING OXAZOLIDINONES TO THEIR CORRESPONDING AMINOALCOHOLS

BACKGROUND OF THE INVENTION

The removal of acid gases such as $H_2S$, $CO_2$, and COS and the like from natural and synthetic gases, including hydrogen, to improve their quality is a widely practiced technology employing many different processes based on chemical reactant and physical absorption characteristics of these acid gases with both liquids and solvents. However, one of the most widely used processes employs nitrogenous alcohols (amino alcohols) alone or in combination with one or more chemical reactants or physical absorbents such as sulfolane. These products of the reaction as well as the absorbents of course must be regenerated, freed of the acid gas, and be reused to absorb the acid gases from the natural or synthetic gas in a cyclical process. During regeneration some of the amino alcohols undergo cyclization in the presence of and in reaction with $CO_2$ to the corresponding oxazolidinone which is difficult to reform into the amino alcohol and release the $CO_2$ during regeneration. The so-formed cyclic amine which remains unchanged creates a waste product of these unusable heavy materials which must be purged from the system to prevent their build-up.

A recent U.S. Pat. No. 3,658,462 addressed itself to a process to regenerate the amino alcohol in large quantities. However, 1 mol of salt per mole of waste cyclical product processed are formed thus while removing the waste product and regenerating the amino alcohol the salt creates a disposal problem.

In a similar fashion, UK Pat. No. 1,118,687 describes contacting aqueous amino alcohol containing waste streams from acid gas purification processes with sufficient alkaline reacting potassium compound, e.g., KOH, to cause separation into a purified amine rich phase and an aqueous potassium salt containing phase. French Brevet No. 2,382,922 addresses the same problem of regenerating such amino alcohols from acid gas treatment solutions, by heating same in the presence of water at elevated temperature and pressure, e.g., 200°–300° C. and 10–60 atmospheres. U.S. Pat. No. 4,138,468 describes like regeneration of amino alcohols by heating at 140°–200° C. in the presence of a gross stoichiometric excess of water for extended periods of time, generally at elevated pressure.

It would be, therefore, advantageous to have a process for converting the cyclic nirogen compounds (the oxazolidinones) back to their corresponding amino alcohols without the generation of the large solids volume of the conventional base conversions, without the use of elevated pressure or indeed without any separate step of separating and treating oxazolidinone "bottoms".

BRIEF DESCRIPTION OF THE INVENTION

In accordance with the present invention it has been found that a small, catalytic, amount of a basic compound such as $K_2CO_3$ or other metal salt capable of conversion to the hydroxide form such as the metal carbonates, hydroxides, acid carbonates, oxides, borates or hydrides particularly the alkali metal and more particularly $K_2CO_3$, added to an aqueous mixture of the so-called "still bottoms" resulting from purging the bottoms (usually about 88+ percent oxazolidinone), diluted with sufficient water to maintain the solids in solution and the resulting reaction mass heated to at least about 120° C., permitting a rise in temperature to about 195° C. over from 20 to 100 hours, usually results in conversion of about fifty or more percent of the oxazolidinone to alkanolamine and $CO_2$. Recovery of the alkanolamine can be accomplished by vacuum distillation. Good results have been observed when from less than 1 up to 10 mole percent of a basic compound is used per mole of oxazolidinone and about 3 mol of water, in addition to that in the reclaimer bottoms, are employed. Following recovery of the alkanolamine after heating, additional oxazolidinone (as reclaimer bottoms) can be added to the reaction mass to convert it to the corresponding amino alcohol equaling conversion of about 79.1% of the total oxazolidinone feed.

In another mode, a catalytic amount of the inorganic base is added to the alkanolamine (and optionally sulfolane) containing absorbent process medium so that formation of oxazolidinones in the $CO_2$ absorption stage or the regeneration stage of the process may be continuously reversed in situ once the reaction mass is heated to at least about 105° C. or higher. In this fashion, the need for separately reclaiming oxazolidinone bottoms and converting them to their corresponding alkanolamines may be obviated.

The invention method is preferably carried out by contacting the oxazolidinone with a small but catalytic amount of an inorganic base in aqueous solution while heating the reactants so as to permit a temperature rise of the reaction medium to a temperature of between about 120° to 200° C. Preferably, the reaction medium is maintained at a temperature between about 120° and about 190° C. for from 20 to 100 hours.

The amount of inorganic base employed is suitably from less than 0.1 up to about 10 mole % based on the oxazolidinone reaction. Preferably less than 5, more preferably less than 2 and most preferably less than 1 mole percent is employed. Preferably more than 0.01, more preferably more than 0.05 and most preferably more than 0.1 mole percent is employed.

The oxazolidinones which are normally treated in accordance with the process of the present invention are those derived from the cyclization of $CO_2$ and, respectively, monoethanolamine, diethanolamine, monoisopropanolamine, or diisopropanolamine or mixtures thereof in a gas conditioning process employing one or more of these amines or a combination of one or more of these amines with this well-known acid gas absorbents such as sulfolane and the like.

DETAILED DESCRIPTION OF THE INVENTION

COMPARATIVE EXAMPLES (A) When 0.224 mol of NaOH in 1.11 mole of water was mixed with 1 mol of 5-methyl-N-(2-hydroxypropyl) oxazolidin-2-one (MHPO) and the mixture heated at 95° C. for five hours there was obtained about a 13 percent conversion of the MHPO to diisopropanolamine (DIPA). After 29 hours at 95° C. only 13.9% conversion was achieved. Following the addition of an additional 0.22 mol of NaOH to the reaction mass, continued heating at 95° C. resulted in a conversion of only about 25%. This experiment establishes that the reaction to convert one mol of MHPO to its component (1 mol diisopropanolamine) requires two (2) mol NaOH.

A white precipitate formed during the process and was identified by IR analysis as $Na_2CO_3$.

(B) In another experiment two equivalents of a 50% NaOH solution was added to reclaimer bottoms, comprising about 88 wt. % MHPO, from a "SULFINOL" process operated in accordance with U.S. Pat. No. 3,347,621 and Shell Technical Bulletin 1C:653 "Shell SULFINOL Process Natural Gas" while the reclaimer bottoms were held at about 140° C. The hydrolysis of the MHPO to diisopropanolamine proceeded as rapidly as the caustic solution addition rate, producing a white precipitate. When about two equivalents of caustic had been added during a 2.8 hour period 97% of the MHPO had been converted to diisopropanolamine. Continued heating for 19.7 hours at 105° C. resulted in an additional 2.2% conversion. On adding water the precipitate which formed during the caustic addition dissolved and the aqueous layer which formed was separated from the organic layer. About 90% of the theoretical diisopropanolamine based on the MHPO converted was recovered from the organic phase. This procedure is very similar to that illustrated in the U.S. Pat. No. 3,658,462. The aqueous layer contained equivalent quantities of $Na_2CO_3$.

(C) In another experiment, a charge of reclaimer bottoms was heated for about 16 hours, at 120° C. and ambient pressure. Less than 0.1% conversion of MHPO to DIPA occurred.

PRESENT INVENTION EXAMPLE

Example 1

To a 250 ml round bottom flask equipped with a magnetic stirrer was added 80.1 g. of reclaimer bottoms from a commercially operated "SULFINOL" process. The reclaimer bottoms was analyzed and found to contain 88.8% MHPO and 8.8% water, the remainder undetermined. The flask and contents were heated to 123° over about one-half hour whereupon 0.71 g. of anhydrous $K_2CO_3$ (1.1 mol percent based on the MHPO) was added. The material was refluxed for 27.5 hours with periodic sampling. After 27.5 hours the conversion was 59% and the liquid temperature in the flash had risen to 189° C. Heating was continued to maintain the temperature at about 190° C. for about 2.5 hours more. The conversion to DIPA of MHPO charged eventually reached 68 mole %. The flask and contents were cooled and distilled under reduced pressure of 70 to 90 mm Hg. The pot temperature ranged from 43° to 195° C. and there was collected 50.9 g. of material which analyzed as 88% by weight diisopropanolamine.

Example 1A

Additional MHPO was added to the flask contents of Example 1 after distillation and the heating procedure repeated. Diisopropanolamine was recovered after heating cycle on distillation. A series of additions of fresh MHPO to the flask after each distillation resulted in similar results establishing the catalytic nature of the potassium carbonate converting MHPO to diisopropanolamine.

Example 2

In a further example of the present invention, an experiment was run in which the reclaimer bottoms was treated in the manner of Example 1 resulting in 51% conversion of the initial charge of 80.2 grams of reclaimer bottoms to which had been added 0.75 g. (about 1.1 mole %) anhydrous $K_2CO_3$. To the reaction medium, at about 190° C., was added incrementally 161 g of reclaimer bottoms over a 48 hour period. The total recovery by distillation was about 77%. Some DIPA remained in the still (reaction vessel). This experiment indicates a continuous process can be operated by adding reclaimer bottoms to the reactor after an initial reaction period while distilling overhead the converted diisopropanolamine (DIPA) product.

Example 3

Other metal salts employed in the manner of Example 1 have been $KBO_2$ which resulted in a 60% conversion (recovered by distillation) in 23 hours and CaO in combination with $K_2CO_3$ (1:2 ratio by weight) 3% total weight which gave 58% conversion (distilled over) in about 17 hours.

A series of reactions conducted under elevated pressures did not result in any significant increase in conversions or reaction rates.

I claim:

1. A method for catalytically converting an oxazolidinone to its respective alkanolamine precursor by driving carbon dioxide from the oxazolidinone, comprising contacting said oxazolidinone with a small but catalytic amount of an inorganic base in aqueous solution and heating the reactants at a temperature of about 105° to about 200° C.

2. The method of claim 1 wherein the inorganic base is the hydroxide, carbonate or bicarbonate of sodium or potassium.

3. The method of claim 1 or 2 wherein the oxazolidinone is 5-methyl-N-(2-hydroxypropyl) oxazolidin-2-one.

4. The method of claim 1 wherein the temperature is about 120°0 to about 190° C.

5. The method of claim 4 wherein the source of the oxazolidinone is the reclaimer bottoms from a gas treating process employing a mixture of sulfolane and an alkanolamine to separate carbon dioxide from a gas stream comprising same.

6. The method of claim 4 which further comprises the steps of thereafter distilling the alkanolamine so produced from the reaction medium and then adding more oxazolidinone and repeating the operations of claim 4.

7. The method of claim 6 wherein the oxazolidinone is 5-methyl-N-(2-hydroxypropyl) oxazolidin-2-one from reclaimer bottoms of a gas treating process and the inorganic base is potassium carbonate.

8. The method of claim 1 wherein the oxazolidinone is contacted with the inorganic base by virtue of the in situ formation of the oxazolidinone in a gas treating process stream employing an aqueous alkanolamine containing a catalytic amount of the inorganic base and, optionally, sulfolane.

9. A method for recovering alkanolamines from the oxazolidinone formed in the reclaimer bottoms of a gas treating process employing a mixture of sulfolane and an alkanolamine to separate carbon dioxide from a natural or synthetic gas or hydrogen, which method comprises a cycle of heating said reclaimer bottoms with a small but catalytic amount of a basic catalytic; compound in sufficient water to dissolve the basic catalyst; periodically distilling the alkanolamine produced in the reaction from the reaction zone; adding additional oxazolidinone to said reaction zone and repeating said cycle; said heating during reaction being to a temperature between about 120° and 190° C.

10. A method for recovering diisopropanolamine from the 5-methyl-N-(2-hydroxypropyl) oxazolidinone (MHPO) in a reclaimer bottoms from a reclaimer of a gas treating process employing an alkanolamine or mixture of alkanolamine with sulfolane to separate carbon dioxide from a natural or synthetic gas or hydrogen which method comprises heating said reclaimer bottoms with about 0.1 to 5 mol % of a basic compound or a compound capable of conversion to a basic compound introduced as a metal salt in sufficient water to maintain the basic catalyst dissolved; periodically distilling the diisopropanolamine produced in the reaction from the reaction zone; adding additional MHPO to said reaction zone and repeating said cycle, said heating during reaction being to a temperature between about 120° to 195° C. for between about 20 to about 100 hours and said distillations being carried out at reduced pressures of between about 70 and 90 mm Hg.

11. A method for recovering diisopropanolamine from the 5-methyl-N-(2-hydroxypropyl) oxazolidinone in a reclaimer bottoms from a reclaimer of a gas treating process employing a mixture of sulfolane and diisopropanolamine to separate carbon dioxide from a natural or synthetic gas or hydrogen which method comprises heating said reclaimer bottoms with about 1 to 10 mol % of a basic compound in sufficient water to maintain the salt of reaction dissolved, periodically distilling the diisopropanolamine produced in the reaction from the reaction zone, adding additional MHPO to said reaction zone and repeating said cycle, said heating during reaction being to a temperature between about 120° and 190° C. for between about 20 to about 100 hours and said distillations being carried out at reduced pressures of between about 70 to 90 mm Hg.

* * * * *

UNITED STATES PATENT AND TRADEMARK OFFICE
CERTIFICATE OF CORRECTION

PATENT NO. : 4,281,200
DATED : July 28, 1981
INVENTOR(S) : Karel A. J. Snoble

It is certified that error appears in the above—identified patent and that said Letters Patent is hereby corrected as shown below:

Column 1, line 51 "nirogen" should be --nitrogen--.

Column 2, line 38 "reaction" should be --reactant--.

Column 3, line 42 "flash" should be --flask--.

Column 4, line 36, Claim 4 "120°0" should be --120°--.

Column 4, line 62, Claim 9 remove the semicolon after catalytic.

Signed and Sealed this

Nineteenth Day of January 1982

[SEAL]

Attest:

GERALD J. MOSSINGHOFF

Attesting Officer — Commissioner of Patents and Trademarks